United States Patent [19]

Matsumura

[11] Patent Number: 4,659,808
[45] Date of Patent: Apr. 21, 1987

[54] PROCESS FOR PRODUCING KETALS OF 2-KETOGULONIC ACID OR ITS ESTERS

[75] Inventor: Koichi Matsumura, Osaka, Japan

[73] Assignee: Takeda Chemical Industries, Ltd., Osaka, Japan

[21] Appl. No.: 654,248

[22] Filed: Sep. 25, 1984

[30] Foreign Application Priority Data

Sep. 28, 1983 [JP] Japan .................. 58-181305

[51] Int. Cl.$^4$ .............................. C07H 1/00
[52] U.S. Cl. .................. 536/18.5; 536/120; 536/124; 536/4.1
[58] Field of Search ............. 536/124, 120, 18.5

[56] References Cited

U.S. PATENT DOCUMENTS 3,139,443  6/1964  Sosnovsky ............ 536/124
3,598,804  8/1971  Hindley et al. ........ 536/124
3,607,862  9/1971  Jaffe et al. ........... 536/124
3,622,506 11/1971  Hindley et al. ........ 536/124
4,460,767  7/1984  Matsumura et al. ..... 536/124
4,464,204  8/1984  Niekamp et al. ....... 536/124
4,464,530  8/1984  Matsumura et al. ..... 536/124

FOREIGN PATENT DOCUMENTS 0076118  9/1982  European Pat. Off. ...... 536/124

Primary Examiner—Johnnie R. Brown
Attorney, Agent, or Firm—Wegner & Bretschneider

[57] ABSTRACT

A novel process is disclosed for production of ketals of 2-ketogulonic acid or of its esters, which comprises reacting 2-ketogulonic acid or its esters with a ketone in the presence of a ketal formation catalyst. The process is advantageous from the industrial point of view to give ketals of 2-ketogulonic acid or of its esters.

13 Claims, No Drawings

PROCESS FOR PRODUCING KETALS OF 2-KETOGULONIC ACID OR ITS ESTERS

This invention relates to a process for producing ketals of 2-ketogulonic acid or of its esters. More particularly, the present invention is concerned with a process for producing 2,3:4,6-di-O-ketals or 2,3-O-ketals of 2-ketogulonic acid or of its esters.

2,3:4,6-Di-O-ketals of 2-ketogulonic acid and those of its esters, as an intermediate in the synthesis of vitamin C, are important as 2-ketogulonic acid and its esters [T. C. Crawford and S. A. Crawford; Advances in Carbohydrate Chemistry and Biochemistry, vol. 37, pp. 89–106 (1980), and U.S. Pat. No. 2,159,191 (1939)]. 2,3-O-Ketals of 2-ketogulonic acid esters also have been known to be useful not only as a synthetic intermediate in the production of vitamin C [British Pat. No. 601,789 and U.S. Pat. No. 2,491,933] but also as a synthetic intermediate for the derivatives of vitamin C [J. Kiss and W. Arnold; Experimentia, vol. 36, pp. 1138 (1980) and J. Kiss and W. Arnold et al.; Helv. Chim. Acta, vol. 63, pp. 1728 (1980)].

2-Ketogulonic acid or its esters, by conversion into their 2,3:4,6-di-O-ketals or 2,3-O-ketals, can yield the compounds which are readily soluble in organic solvents such as benzene, toluene, acetone, dichloromethane, chloroform, ether and dioxane, and this can likewise be employed as a procedure for purifying 2-ketogulonic acid and its esters.

Conventionally, 2,3:4,6-di-O-ketals of 2-ketogulonic acid have been synthesized by subjecting a 2,3:4,6-di-O-ketal of sorbose to a reaction such as chemical oxidation with potassium permanganate, sodium hypochlorite, etc., air oxidation with use of a platinum catalyst, etc. or electrochemical oxidation [T. C. Crawford and S. A. Crawford; Advances in Carbohydrate Chemistry and Biochemistry, vol. 37, pp. 93–96 (1980)]. 2,3:4,6-di-O-Isopropylidene derivatives of 2-ketogulonic acid esters can be produced also by air oxidation reaction of 2,3:4,6-di-O-isopropylidene derivatives of sorbose in the presence of alcohol (The Japanese Unexamined Patent Publication No. 94395/1980).

On the other hand, 2,3-O-isopropylidene derivatives of 2-ketogulonic acid esters have been synthesized by partial hydrolysis reaction of 2,3:4,6-di-O-isopropylidene derivatives of 2-ketogulonic acid esters [J. Kiss, W. Arnold, et al.; Helv. Chim. Acta, vol. 63, pp. 1728 (1980)] or by the esterification reaction accompanied with partial hydrolysis reaction of the 4,6-O-isopropylidene group in 2,3:4,6-di-O-isopropylidene derivatives of 2-ketogulonic acid esters [British Pat. No. 601,789 and U.S. Pat. No. 2,491,933].

The present inventor attempted to conduct a reaction of 2-ketogulonic acid or its ester with a ketone, which is different from the above-mentioned known processes, and found that said reaction in the presence of a ketal formation catalyst proceeds favorably from the industrial point of view to give a ketal of 2-ketogulonic acid or of its ester, and this has culminated into the present invention.

Thus, the present invention is directed toward a process for producing ketals of 2-ketogulonic acid or of its esters, which comprises reacting 2-ketogulonic acid or its ester with a ketone in the presence of a ketal formation catalyst.

In the present invention, use is made of 2-ketogulonic acid or its esters as a starting compound. The groups constituting said esters are not specifically restricted, unless they inhibit the present ketal formation reaction, but their specific examples include alkyl, cycloalkyl, alkenyl and aralkyl groups, which each are exemplified by the following:

As the alkyl group, there may be mentioned those having a carbon number in the range of 1 to 18, such as methyl, ethyl, propyl, i-propyl, butyl, i-butyl, sec-butyl, t-butyl, pentyl, neopentyl, hexyl, heptyl, octyl, nonyl, decyl, undecyl, dodecyl, tetradecyl, pentadecyl, hexadecyl, heptadecyl and octadecyl; as the cycloalkyl group, by way of example, there may be mentioned cyclobutyl, cyclopentyl, cyclohexyl, cycloheptyl and cyclooctyl; as the alkenyl group, there may be mentioned those having a carbon number of 3 to 14 such as 2-propenyl and 2-methyl-2-propenyl groups; and as the aralkyl group, by way of example, there may be mentioned groups having an aryl group substituted by alkyl group with a carbon number in the range of 1 to 4 (e.g., benzyl, phenethyl, 1-phenylethyl, 1- or b 3-phenylpropyl, 1-methyl-3-phenylpropyl, 4-phenylbutyl), such aryl groups being typified by the phenyl, furyl, thienyl and pyridyl groups which may be substituted by lower alkyl and lower alkoxy groups, halogens, etc.

2-Ketogulonic acid esters are obtained by reacting 2-ketogulonic acid with an alcohol having the above-mentioned alkyl, cycloalkyl, alkenyl or aralkyl group in the presence of an acid catalyst according to the conventionally known method or a method similar thereto.

The ketone being usable in the present invention is not specifically restricted, but use is preferably made of those having a carbon number of 3 to 7, of which specific examples include a dialkyl ketone having a carbon number of 3 to 6 such as acetone, methyl ethyl ketone, diethyl ketone, di-n-propyl ketone and di-i-propyl ketone; and a cyclic ketone having a carbon number of 5 to 7 such as cyclopentanone, cyclohexanone and cycloheptanone. The amount of these ketones to be used is at least 2 to 10 times of the theoretical molar quantity, but it is normally advantageous to use these ketones in large excess as the reaction reagent and solvent.

The reaction in the production process according to the present invention is carried out in the presence of a ketal formation catalyst. As the said catalyst, use can be made of any catalyst that promotes the ketal formation reaction, but generally, halides and other acid catalysts are suitable. Specifically, there may be mentioned fluorine-containing catalysts, chlorine-containing catalysts, bromine-containing catalysts, iodine-containing catalysts, etc. as being exemplified in the following:

As the fluorine-containing catalyst, there may be mentioned hydrogen fluoride, hydrogentetrafluoroborate, fluorosulfuric acid, trifluoromethanesulfonic acid, H type ion exchange resins having perfluorosulfonic acid residues being typified by Nafion-H ®, perfluorocarboxylic acids being represented by trifluoroacetic acid, acid fluorides being typified by formyl fluoride and acetyl fluoride, sulfonyl fluorides being represented by methanesulfonyl fluoride, sulfuryl fluorochloride, fluorine monochloride, fluorine monobromide, fluorine monoiodide, boron trifluoride, boron trifluoride.ether complex, antimony pentafluoride, molybdenum fluoride, arsenic pentafluoride, etc.

As the chlorine-containing catalyst, there may be mentioned hydrogen chloride, perchloric acid, trichloroacetic acid, acid chlorides being typified by formyl chloride and acetyl chloride, phosgene, thionyl chloride, sulfuryl chloride, sulfonyl chlorides being represented by methanesulfonyl chloride, trimethylsilyl chloride, boron trichloride, ammonium chloride, aluminum chloride, silicon tetrachloride, phosphorus trichloride, phosphorus oxychloride, phosphorus pentachloride, sulfur monochloride, sulfur dichoride, chlorine, N-chlorosuccinimide, calcium chloride, titanium tetrachloride, ferric chloride, cupric chloride, zinc chloride, gallium perchlorate.hydrate, germanium tetrachloride, zirconium tetrachloride, rhodium chloride, palladium chloride, stannic chloride, stannous chloride, antimony pentachloride, antimony trichloride, molybdenum pentachloride, tantalum pentachloride, tungsten hexachloride, lanthanum chloride, cerium chloride, neodymium chloride, erbium chloride, ytterbium chloride, and so forth.

As the bromine-containing catalyst, there may be mentioned N-bromosuccinimide, acid bromides represented by acetyl bromide, sulfonyl bromides typified by methane sulfonyl bromide, bromine, trimethylsilyl bromide, boron tribromide, ammonium bromide, aluminum bromide, phosphorus tribromide, phosphorus pentabromide, ferric bromide, cupric bromide, zinc bromide, stannic bromide, stannous bromide, titanium bromide, cerium bromide, etc.

Although hydrogen fluoride, hydrogen chloride and hydrogen bromide each can be employed solely, their catalytic activities can be enhanced by copper, iron, or their oxides, hydroxides or salts.

As the above-mentioned copper, there may be mentioned copper powder; examples of the said oxides of copper include cuprous oxide and cupric oxide; examples of said hydroxides of copper include cuprous hydroxide and cupric hydroxide; and as the said salts of copper, by way of example, there may be mentioned (a) copper halides (e.g., cuprous halides such as cuprous chloride, cuprous bromide and cuprous iodide, and cupric halides such as cupric chloride, cupric bromide and cupric fluoride), (b) inorganic acid salts of copper (e.g., cuprous sulfide, cuprous cyanide, cuprous thiocyanate, cupric sulfide, copper borofluoride, copper silicofluoride, copper arsenite, copper perchlorate, copper sulfate, cupric phosphate, cupric pyrophosphate, cupric cyanide, cupric thiocyanate, etc.), (c) organic acid salts of copper (e.g., copper formate, copper acetate, copper oxalate, copper citrate, copper benzoate, copper oleate, copper stearate, copper acetylacetonate, etc.) and (d) double salts of copper (e.g., basic copper carbonate, potassium cupric chloride, calcium copper acetate, copper oxychloride, ammonium cupric chloride, etc.)

As the said iron, there may be mentioned iron powder; examples of the said oxides of iron include ferrous oxide, ferric oxide and triiron tetroxide; examples of the said hydroxides of iron include ferric hydroxide; and as the said salts of iron, by way of example, there may be mentioned (a) iron halides (e.g., ferrous halides such as ferrous chloride, ferrous bromide, ferrous iodide and ferrous fluoride, ferric halides such as ferric chloride, ferric bromide and ferric fluoride, etc.), (b) inorganic acid salts of iron (e.g., iron sulfide, iron silicofluoride, iron borofluoride, ferrous thiocyanate, ferrous perchlorate, ferrous sulfate, ferrous phosphate, ferric thiocyanate, ferric perchlorate, ferric sulfate, ferric nitrate, ferric phosphate, ferric pyrophosphate, etc.), (c) organic acid salts of iron (e.g., ferrous oxalate, ferrous fumarate, ferrous lactate, iron acetate, ferric oxalate, ferric tartarate, ferric citrate, ferric acetylacetonate, etc.) and (d) double salts of iron (e.g., ammonium ferrous sulfate, ammonium ferric sulfate, potassium ferric sulfate, ammonium iron citrate, ammonium ferric oxalate, etc.).

As the iodine-containing catalyst, use may be made of hydrogen iodide as such or in the form of hydriodic acid produced by dissolving hydrogen iodide in water, or compounds existing in the form of hydrogen iodide in the reaction system or systems liberating hydrogen iodide in the reaction system.

Examples of the above-mentioned compounds existing in the form of hydrogen iodide in the reaction system or systems liberating hydrogen iodide in the reaction system include (1) metal iodides and acids, (2) iodinating agents, (3) iodinating agents and reducing agents and (4) Lewis acids containing iodine. Specific examples of the said metal iodides include sodium iodide, potassium iodide, magnesium iodide, calcium iodide, ammonium iodide and lead iodide; as the said acids, there may be mentioned for example phosphoric acid, nitric acid, sulfuric acid, hydrochloric acid, hydrobromic acid, trifluoroacetic acid and perchloric acid; as the said iodinating agents, there may be mentioned for example iodine, iodine monochloride, iodine monobromide, iodine trichloride, phosphorus iodide, N-iodosuccinimide and trimethylsilyl iodide; and examples of the said reducing agents include hydrogen sulfide, hypophosphrous acid, sulfurous acid, hydrazine, L-ascorbic acid and D-erythorbic acid.

As the Lewis acid containing iodide, there may be mentioned aluminum iodide, boron iodide, stannic iodide, titanium iodide, etc. Other iodine-containing catalysts include zinc iodide, palladium iodide, stannous iodide, cerium iodide, and so forth.

In addition to those described above, as other acid catalysts, use can also be made of nitric acid, phosphoric acid, sulfuric acid, p-toluenesulfonic acid, benzenesulfonic acid, sulfosalicyclic acid, naphthalenesulfonic acid, methanesulfonic acid, H type ion exchange resins, acetic acid, oxalic acid, phosphrus pentoxide, ethyl metaphosphate, copper sulfate and so forth.

The above-mentioned ketal formation catalysts may be either in the form of anhydride or crystals or in the form of hydrate according to their types. The amount of catalyst to be used is within the range of about 0.01 to 100 weight % relative to the amount of 2-ketogulonic acid or its ester, whereby not less than two kinds of the catalysts may be employed in combination at a suitable weight ratio.

In the production process according to the present invention, among the above-mentioned catalysts, it is particularly preferred to use hydrogen iodide, antimony pentachloride, antimony pentafluoride, trifluoromethanesulfonic acid, cupric chloride or cupric bromide in the range of about 0.01 to 10 weight %, preferably about 0.05 to 5 weight %, or to employ about 0.01 to 30 weight %, preferably about 0.05 to 10 weight %, of hydrogen chloride or hydrogen bromide in the presence of the nearly equal amount of copper, iron or their oxides, hydroxides or salts, all relative to the weight of 2-ketogulonic acid or its esters.

As the reaction solvent being usable in the production process of the present invention, use can be made of any solvent, unless it inhibits the reaction, and there may be mentioned acetonitrile, propionitrile, nitromethane, nitroethane, nitrobenzene, dichloromethane, chloroform, carbon tetrachloride, 1,1-dichloroethane, 1,2-dichloroethane, ethyl bromide, pentane, cyclopentane, hexane, cyclohexane, heptane, benzene, toluene, xylene, dimethylformamide, dimethylsulfoxide, etc. Furthermore, the above-mentioned ketones can also be used as solvent in addition to reactant, and the reaction can be carried out in a mixed solvent consisting of not less than two kinds of these solvents, as well. Moreover, in order to increase the solubilities of sugar and catalyst in the said solvents, a small amount of water may be added at the time of initiation of reaction.

Since the present reaction is an equilibrium reaction and removal of the water produced in the reaction generally results in an improved yield in the case of production of 2,3,:4,6-di-O-ketals of 2-ketogulonic acid or of its esters, the reaction may be conducted while removing the water from the reaction system in accordance with the known procedure. As the known procedure in this case, there may be mentioned the distillation of the water or use of drying agents, etc. In the case of distillation of the water, the method utilizing the azeotropy between solvent and water is commonly employed, wherein the water may be separated and removed from the liquid produced by cooling the vapor distilled under azeotropy, with the remaining solvent being returned to the reaction vessel, or the azeotropic vapor may be removed out of the reaction system, with the equal amount of dry solvent being added anew to the reaction system. As the procedure using drying agents, the azeotropic vapor, directly or after being cooled to convert into liquid, may be dried with a drying agent typified by anhydrous calcium sulfate, molecular sieves, alumina, etc. and subsequently returned to the reaction vessel.

Since removal of the water in the reaction system leads rather to a decreased yield in the case of production of 2,3-O-ketals of 2-ketogulonic acid or of its esters, on the other hand, elimination of the above procedure of removing the water is desirable for the purpose of increasing the yields of the said 2,3-O-ketals in the reaction product, and a small amount of water may be added to the reaction system, as the case may be.

The reaction temperature is normally in the range of about 0° C. to 150° C., preferably in the range of about 20° C. to 100° C. In order to adjust the azeotropic point of the solvent or ketone and water, the reaction may be carried out under reduced pressure.

The reaction time varies depending upon the types of 2-ketogulonic acid or its esters and ketones, kind and amount of the catalysts and reaction conditions, but is normally in the range of about 30 minutes to 10 hours, preferably in the range of about 1 hour to 8 hours.

In order to isolate the ketals of 2-ketogulonic acid or of its esters thus obtained from the reaction system, the reaction solvent may be distilled off either as such or after the addition of a small amount of alkali (e.g., sodium bicarbonate, potassium bicarbonate, sodium carbonate, potassium carbonate, sodium hydroxide, potassium hydroxide, ammonia, pyridine) or an aqueous solution of the said alkali. By subjecting the resulting residue to the known means such as extraction, distillation, column chromatography or recrystallization, the objective 2,3:4,6-di-O-ketals or (and) 2,3-O-ketals of 2-ketogulonic acid or its esters can be easily obtained.

As having been described in the above, the present invention provides a novel process for producing 2,3:4,6-di-O-ketals or (and) 2,3-O-ketals of 2-ketogulonic acid or of its esters in a high yield, which comprises allowing the so far unknown ketal formation reaction to proceed advantageously from the industrial point of view through the reaction between 2-ketogulonic acid or its esters and ketone.

The examples are described below to illustrate the present invention in more detail.

EXAMPLE 1

To 300 ml of acetone were added 20.0 g of 2-keto-L-gulonic acid monohydrate and 337 mg of 57% hydriodic acid, and the mixture was refluxed in water bath of 60° C. for 8 hours. During this reaction, the refluxing solvent was dried with 35 g of Molecular Sieves 3A (synthetic zeolite produced by Wako Pure Chemical Industries, Ltd. Japan, average pore diameter; ca. 3A) interposed between the reaction vessel and the condenser. After completion of the reaction, a small amount of pyridine was added to the reaction solution, and the solvent was distilled off under reduced pressure. The residue was dissolved in 300 ml of benzene, and the solution was placed in a separating funnel. After the addition of 100 ml of 5% aqueous solution of caustic soda, the extraction was conducted, and the water layer was separated. Furthermore, 20 ml of 5% caustic soda was added, and the same procedure was repreated twice. Hydrochloric acid was added dropwise, for neutralization, to the resulting caustic soda extract, and the precipitate was recovered by filtration, washed with a small amount of cold water and dried to give 25.35 g (92.0%) of 2,3,:4,6-di-O-isopropylidene-2-keto-L-gulonic acid monohydrate.

Melting point, 99°–100° C. (decomposition) (recrystallized from acetonitrile).

IR (KBr) cm$^{-1}$: 3380, 1730, 1712.

NMR (DMSO-d$_6$) δ: 1.20(s, 3H), 1.31(s, 3H), 1.36(s, 3H), 1.42(s, 3H), 3.6–4.2(m, 3H), 4.2–4.3(m, 1H), 4.63(s, 1H), 4.8–6.5(br. 3H).

Elemental analysis (%), for $C_{12}H_{20}O_8$ Calcd.: C, 49.31; H, 6.90. Found: C, 49.22; H, 7.05.

EXAMPLE 2

To 200 ml of acetone were added 10.0 g of 2-keto-L-gulonic acid monohydrate and 224.6 mg of 57% hydriodic acid, and the refluxing was continued in a water bath of 60° C. for 7 hours. After completion of the reaction, 2.30 g of the insoluble starting material was recovered by filtration, and the filtrate was concentrated to dryness under reduced pressure. The residue was purified by subjecting to silica-gel column chromatography to give 5.30 g (38.5%) of 2,3:4,6-di-O-isopropylidene-2-keto-L-gulonic acid monohydrate and 3.21 g (30.2%, in the form of syrup) of 2,3-O-isopropylidene-2-keto-L-gulonic acid. The structure of 2,3-O-isopropylidene-2-keto-L-gulonic acid was confirmed by the IR and NMR data as shown in the below.

IR (neat) cm$^{-1}$: 3400, 1745.

NMR (DMSO-d$_6$) δ: 1.30(s, 3H), 1.43(s, 3H), 3.55–3.64(1H), 3.93–4.07(m, 3H), 4.63(s, 1H), 3.5–7.0(br., 3H)

EXAMPLE 3

To 200 ml of acetone were added 10.0 g of 2-keto-L-gulonic acid monohydrate and each of the catalysts as shown in Table 1, and the mixture was refluxed in a water bath of 60° C. for 8 hours. During this reaction, the refluxing solvent was dried with 20 g of Molecular Sieves 3A interposed between the reaction vessel and the condenser. After completion of the reaction, the total volume of the reaction solution was made up to 200 ml, and 2,3:4,6-di-O-isopropylidene-2-keto-L-gulonic acid monohydrate was determined by high performance liquid chromatography (column: Shimadzu Zolbacks BP-NH₂ 4 mm×25 cm; mobile phase: 75% CH₃CN-25% H₂O containing 0.005 mol/l of KH₂PO₄ 1.5 ml/min; detector; UV (210 nm)), yielding the results as shown in Table 1. In every cases, there were obtained about 3 to 5% of 2,3-O-isopropylidene-2-keto-L-gulonic acid as a by-product (as calculated from the peak areas of the high performance liquid chromatograms.

TABLE 1

| No. | Catalyst | 2,3:4,6-Di-O—isopropylidene-2-keto-L-gulonic acid monohydrate | | |
|---|---|---|---|---|
| | | mg | g | Yield (%) |
| 1 | HI*¹ | 224.6 | 13.02 | 94.5 |
| 2 | I₂ | 76.2 | 12.77 | 92.7 |
| 3 | I₂ | 127 | 13.06 | 94.8 |
| 4 | ICl | 162.5 | 7.12 | 91.5*² |
| 5 | ICl₃ | 233.5 | 8.12 | 92.8*³ |
| 6 | IBr | 207 | 12.41 | 90.1 |
| 7 | P₂I₄ | 114 | 12.81 | 93.0 |
| 8 | N—iodo-succinimide | 225 | 12.41 | 90.1 |
| 9 | TiI₄ | 166.5 | 12.21 | 88.6 |
| 10 | BI₃ | 117.6 | 12.59 | 91.4 |
| 11 | SbCl₅ | 89.7 | 12.50 | 90.7 |
| 12 | SbF₅ | 65.0 | 13.02 | 94.5 |
| 13 | CuBr₂ | 111.3 | 11.89 | 86.3 |
| 14 | CuCl₂.2H₂O | 170.5 | 11.79 | 85.6 |
| 15 | FeBr₃ | 295.8 | 4.95 | 80.5*⁴ |
| 16 | CF₃SO₃H | 75.0 | 12.59 | 91.4 |
| 17 | BF₃.OEt₂*⁵ | 148.1 | 11.43 | 83.0 |

*¹57% hydriodic acid was used.
*²Yield based on the consumed starting material (4.35 g of starting material was recovered)
*³Yield based on the consumed starting material (3.65 g of starting material was recovered)
*⁴Yield based on the consumed starting material (5.54 g of starting material was recovered)
*⁵47% solution was used.

EXAMPLE 4

To a mixed solution consisting of 250 ml of diethyl ketone and 150 ml of dichloromethane were added 20.0 g of 2-keto-L-gulonic acid monohydrate and 561 mg of 57% hydriodic acid, and the mixture was refluxed in a water bath of 70° C. for 8 hours. During this reaction, the refluxing solvent was dried with 35 g of Molecular Sieves 3A interposed between the reaction vessel and the condenser. After completion of the reaction, the reaction solution was cooled, and 8.90 g of the insoluble material (starting material) was filtered off. The solvent was distilled off under reduced pressure, and the residue was dissolved in 300 ml of benzene, which was transferred to a separating funnel. After the procedure of extraction was conducted twice with 100 ml of 5% aqueous caustic soda solution, the alkali extract was neutralized with hydrochloric acid under ice-cooling, and the precipitate was recovered by filtration, washed with a small amount of water and dried to give 14.42 g (83.4%, based on the consumed starting material) of 2,3:4,6-di-O-(3-pentylidene)-2-keto-L-gulonic acid.

Melting point, 149°-149.5° C. (recrystallized from benzene-n-hexane).

IR (KBr) cm⁻¹: 1745.

NMR (DMSO-d₆) δ: 0.5-1.1(m, 12H), 1.2-2.1(m, 8H), 3.7-4.4(m, 4H), 4.70(s, 1H), 13.6(br., 1H).

Elemental analysis (%), for C₁₆H₂₆O₇ Calcd.: C, 58.17; H, 7.93. Found: C, 58.41; H, 7.88.

EXAMPLE 5

To a mixed solution consisting of 150 ml of diethyl ketone and 100 ml of dichloromethane were added 10.0 g of 2-keto-L-gulonic acid monohydrate and 108.4 mg of antimony pentafluoride, and the mixture was refluxed in a water bath of 70° C. for 8 hours. During this reaction, the refluxing solvent was dried with 20 g of Molecular Sieves 3A interposed between the reaction vessel and the condenser. After completion of the reaction, the reaction solution was cooled, and 1.73 g of the insoluble material (starting material) was filtered off. The low-boiling substances were distilled off under reduced pressure, and the residue was dissolved in CH₃CN-H₂O (75:25 V/V) to make the total volume up to 200 ml. The quantitative analysis of this solution according to the procedure as described in Example 3 indicated that there was obtained 12.24 g (95.0%, based on the consumed starting material) of 2,3:4,6-di-O-(3-pentylidene)-2-keto-L-gulonic acid and 0.30 g (2.4%) of 2,3-O-(3-pentylidene)-2-keto-L-gulonic acid.

Melting point, 140°-142° C. (recrystallized from ethyl acetate-n-hexane).

IR (KBr) cm⁻¹: 3400, 1745

NMR (DMSO-d₆) δ: 0.7-1.05(m, 6H), 1.4-2.0(m, 4H), 3.55-3.8(2H), 4.0-4.4(3H), 4.65(s, 1H), 4.7-7.5 (very broad, 2H).

Elemental analysis (%), for C₁₁H₁₈O₇ Calcd.: C, 50.38; H, 6.92. Found: C, 50.57; H, 7.06.

EXAMPLE 6

To a mixed solution consisting of 250 ml of cyclopentanone and 150 ml of dichloromethane were added 20.0 g of 2-keto-L-gulonic acid monohydrate and 177.8 mg of iodine, and the mixture was refluxed in a water bath of 70° C. for 8 hours. During this reaction, the refluxing solvent was dried with 35 g of Molecular Sieves 3A interposed between the reaction vessel and the condenser. After completion of the reaction, a small amount of pyridine was added to the reaction solution, and the low-boiling substances were distilled off under reduced pressure. The residue was dissolved in 300 ml of benzene, and the solution was transferred to a separating funnel. The solution was extracted with 200 ml of 5% aqueous caustic soda. Furthermore, the solution was extracted twice with 100 ml of 5% aqueous caustic soda. Hydrochloric acid was added dropwise to the alkali extract under ice-cooling for neutralization until it was made slightly acidic, and the resulting precipitate was recovered by filtration, washed with a small amount of cold water and dried to give 27.46 g (84.6%) of 2,3:4,6-di-O-cyclopentylidene-2-keto-L-gulonic acid monohydrate.

Melting point, 75° C. (recrystallized from benzene-n-hexane).

IR (KBr) cm⁻¹: 3400, 1728, 1720.

NMR (DMSO-d₆) δ: 1.3-2.15(br.,16H), 3.85-4.2(m, 3H), 4.2-4.35(m, 1H), 4.61(s, 1H), 6.0(br., 3H).

Elemental analysis (%), for C₁₆H₂₄O₈ Calcd.: C, 55.81; H, 7.02. Found: C, 56.03; H, 6.96.

EXAMPLE 7

To a mixed solution consisting of 200 ml of cyclohexanone and 150 ml of dichloromethane were added 20.0 g of 2-keto-L-gulonic acid monohydrate and 299 mg of antimony pentachloride, and the mixture was refluxed in a water bath of 70° C. for 8 hours. During this reaction, the refluxing solvent was dried with 35 g of Molecular Sieves 3A interposed between the reaction vessel and the condenser. After completion of the reaction, the after-treatment similar to that as described in Example 6 yielded 30.47 g (91.2%) of 2,3:4,6-di-O-cyclohexylidene-2-keto-L-gulonic acid.

Melting point, 128.5°–130.0° C. (recrystallized from benzene-n-hexane).

IR (KBr) cm$^{-1}$: 1780, 1744.

NMR (DMSO-d$_6$) δ: 1.1–2.1(br.,20H), 3.6–4.35(m, 4H), 4.65(s, 1H), 5.5(br., 1H).

Elemental analysis (%), for C$_{18}$H$_{26}$O$_7$ Calcd.: C, 61.00; H, 7.39. found: C, 60.85; H, 7.55.

EXAMPLE 8

To a mixed solution consisting of 200 ml of cyclohexanone and 150 ml of dichloromethane were added 20.0 g of 2-keto-L-gulonic acid monohydrate and 449 mg of 57% hydriodic acid, and the reaction and the after-treatment were carried out by the procedures similar to those as described in Example 7 to give 29.67 g (88.8%) of 2,3:4,6-di-O-cyclohexylidene-2-keto-L-gulonic acid.

EXAMPLE 9

To 200 ml of acetone were added 10.0 g of methyl 2-keto-L-gulonate and 112.3 mg of 57% hydriodic acid, and the mixture was refluxed in a water bath of 60° C. for 8 hours. During this reaction, the refluxing solvent was dried with 20 g of Molecular Sieves 3A interposed between the reaction vessel and the condenser. After completion of the reaction, a small amount of pyridine was added to the reaction solution, and the solvent was distilled off under reduced pressure to give an oily residue. For the purpose of purification, the residue was chromatographed on a silica-gel column (solvent: chloroform) to give 13.18 g (95.2%) of methyl 2,3:4,6-di-O-isopropylidene-2-keto-L-gulonate.

Melting point, 46°–47° C. (recrystallized from n-hexane).

IR (KBr) cm$^{-1}$: 1745.

NMR (CDCl$_3$) δ: 1.30(s, 3H), 1.40(s, 6H), 1.50(s, 3H), 3.80(s, 3H), 3.98–4.4(M, 4H), 4.77(s, 1H).

Elemental analysis (%), for C$_{13}$H$_{20}$O$_7$ Calcd.: C, 54.16; H, 6.99. Found: C, 54.20; H, 7.10.

EXAMPLE 10

To 200 ml of acetone were added methyl 2-keto-L-gulonate and 50.8 mg of iodine, and the refluxing was continued in a water bath of 60° C. for 8 hours. After completion of the reaction, a small amount of pyridine was added to the reaction solution, and the solvent was distilled off under reduced pressure. The residue was chromatographed on a silica gel column (solvent: chloroform) to give 9.09 g (65.6%) of methyl 2,3:4,6-di-O-isopropylidene-2-keto-L-gulonate and 3.02 g (25.3%) of methyl 2,3-O-isopropylidene-2-keto-L-gulonate. Methyl 2,3-O-isopropylidene-2-keto-L-gulonate was confirmed by the analytical data of IR, NMR and elemental analysis to be shown in the following.

Melting point, 65°–68° C. (for the substance solidified from the product purified by chromatography).

IR (KBr) cm$^{-1}$: 3400, 1750.

NMR (DMSO-d$_6$) δ: 1.30(s, 3H), 1.43(s, 3H), 3.30(br., 1H), 3.4–3.75(br., 2H), 3.70(s, 3H), 4.67(br., 1H), 5.17(br., 1H).

Elemental analysis (%), for C$_{10}$H$_{16}$O$_7$ Calcd.: C, 48.39; H, 6.50. Found: C, 48.45; H, 6.44.

EXAMPLE 11

To 200 ml of acetone were added 10.0 g of methyl 2-keto-L-gulonate and each of the catalysts as shown in Table 2, and the mixture was refluxed in a water bath of 60° C. for 8 hours. During this reaction, the refluxing solvent was dried with 20 g of Molecular Sieves 3A interposed between the reaction vessel and the condenser. After completion of the reaction, a small amount of pyridine was added to the reaction solution, and the total volume was made up to 200 ml. The quantitative analysis was conducted by gas chromatography (column: 3% Silicon OV-17 (Nishio Sangyo, Co., Japan), on Uniport HPS (Gasukuro Kogyo Co. Ltd., Japan) 3 m; 210° C. of column temperature), and the results as shown in Table 2 were obtained. It should be noted that in addition to the methyl 2,3:4,6-di-O-isopropylidene-2-keto-L-gulonate, in every cases, there was about 2 to 6% of methyl 2,3-O-isopropylidene-2-keto-L-gulonate.

TABLE 2

| No. | Catalyst | Methyl 2,3:4,6-di-O—isopropylidene-2-keto-L-gulonate | | |
|---|---|---|---|---|
| | | mg | g | Yield (%) |
| 1 | I$_2$ | 50.8 | 12.58 | 90.8 |
| 2 | IBr | 62.1 | 11.26 | 81.3 |
| 3 | PI$_3$ | 41.2 | 12.64 | 91.3 |
| 4 | P$_2$I$_4$ | 57.0 | 12.46 | 90.0 |
| 5 | N—iodo-succinimide | 112.5 | 12.26 | 88.5 |
| 6 | TiI$_4$ | 55.5 | 12.91 | 93.2 |
| 7 | SbCl$_5$ | 59.8 | 12.49 | 90.2 |
| 8 | SbF$_5$ | 43.4 | 12.88 | 93.0 |
| 9 | CF$_3$SO$_3$H | 30.0 | 13.02 | 94.0 |
| 10 | HClO$_4$ | 30.0 | 11.95 | 86.3 |
| 11 | SnCl$_4$ | 260.7 | 10.98 | 78.6 |
| 12 | H$_2$SO$_4$ | 196.0 | 11.09 | 80.1 |
| 13 | RhCl$_3$ | 138.4 | 11.44 | 82.6 |
| 14 | CeCl$_3$.7H$_2$O | 372.6 | 11.15 | 80.5 |
| 15 | FeCl$_3$ | 82.3 | 11.87 | 85.7 |

EXAMPLE 12

To a mixed solution consisting of 150 ml of cyclopentanone and 150 ml of dichloromethane were added 10.0 g of methyl 2-keto-L-gulonate and 127 mg of iodine, and the reaction and the after-treatment were carried out by the procedures similar to those as described in Example 9 to give 14.09 g (86.2%) of methyl 2,3:4,6-di-O-cyclopentylidene-2-keto-L-gulonate.

Melting point, an oily substance.

IR (neat) cm$^{-1}$: 1765sh, 1750.

NMR (CDCl$_3$) δ: 1.4–2.1(br.,16H), 3.83(s, 3H), 3.95–4.35 (m, 4H), 4.78(s, 1H).

Elemental analysis (%), for C$_{17}$H$_{24}$O$_7$ Calcd.: C, 59.99; H, 7.08. Found: C, 59.59; H, 6.90.

EXAMPLE 13

To a mixed solution consisting of 150 ml of cyclohexanone and 150 ml of dichloromethane were added 10.0 g of methyl 2-keto-L-gulonate and 224.6 mg of 57% hydriodic acid, and the reaction and the after-treatment were carried out by the procedures similar to those as described in Example 9 to give 16.81 g (95.0%) of methyl 2,3:4,6-di-O-cyclohexylidene-2-keto-L-gulonate.

Melting point, an oily substance.

IR (neat) cm$^{-1}$: 1748.

NMR (CDCl$_3$) δ: 1.1–2.2(br.,20H), 3.80(s, 3H), 3.95–4.35(m, 4H), 4.78(s, 1H).

Elemental analysis (%), or C$_{19}$H$_{28}$O$_7$ Calcd.: C, 61.94; H, 7.66. Found: C, 61.65; H, 7.94.

EXAMPLE 14

To 100 ml of acetone were added 5.0 g of ethyl 2-keto-L-gulonate and 89.8 mg of 57% hydriodic acid, and the reaction and the after-treatment were carried out by the procedures similar to those as described in Example 9 to give 5.36 g (78.8%) of ethyl 2,3:4,6-di-O-isopropylidene-2-keto-L-gulonate.

Melting point, 100°–101° C. (recrystallized from n-hexane).

IR (KBr) cm$^{-1}$: 1745.

NMR (CDCl$_3$) δ: 1.2–1.65(m, 15H), 4.03–4.55(m, 6H), 4.85(s, 1H).

Elemental analysis (%), for C$_{14}$H$_{22}$O$_7$ Calcd.: C, 55.57; H, 7.33. Found: C, 55.60; H, 7.45.

EXAMPLE 15

A mixture consisting of 10.0 g of 2-keto-L-gulonic acid monohydrate, 200 ml of allyl alcohol and 95.1 mg of p-toluene sulfonic acid monohydrate was allowed to react at 100° C. for 5 hours, and the resulting reaction product was freed of the low-boiling substances under reduced pressure to give allyl 2-keto-L-gulonate.

Melting point, an oily substance.

IR (neat) cm$^{-1}$: 3400, 1745.

NMR (CDCl$_3$) δ: 3.5–6.5(m, 14H).

To 100 ml of acetone were added 5.80 g of allyl 2-keto-L-gulonate and 67.4 mg of 57% hydriodic acid, and the reaction and the after-treatment were carried out by the procedures similar to those as described in Example 9 to give 5.51 g (70.8%) of allyl 2,3:4,6-di-O-isopropylidene-2-keto-L-gulonate.

Melting point, 94°–95° C. (recrystallized from n-hexane).

IR (KBr) cm$^{-1}$: 1753.

NMR (CDCl$_3$) δ: 1.35(s, 3H), 1.45(s, 6H), 1.55(s, 3H), 4.0–4.4(m, 4H), 4.7–4.9(m, 3H), 5.1–6.0(M, 3H).

Elemental analysis (%), for C$_{15}$H$_{22}$O$_7$ Calcd.: C, 57.32; H, 7.05. Found: C, 57.53; H, 7.14.

EXAMPLE 16

To a mixed solution consisting of 100 ml of cyclohexanone and 100 ml of chloroform were added 5.0 g of n-butyl 2-keto-L-gulonate and 14.4 mg of 70% perchloric acid, and the mixture was refluxed in a water bath of 80° C. for 8 hours. During this reaction, the refluxing solvent was dried with 20 g of Molecular Sieves 3A interposed between the reaction vessel and the condenser. After completion of the reaction, a small amount of pyridine was added to the reaction solution, and the solvent was distilled off under reduced pressure. The resulting oily material was chromatographed on a column of silica gel (solvent: chloroform) to give 6.91 g (84.3%) of n-butyl 2,3:4,6-di-O-cyclohexylidene-2-keto-L-gulonate.

Melting point, an oily substance.

IR (neat) cm$^{-1}$: 1740.

NMR (CDCl$_3$) δ: 0.96(t, 3H), 1.2–2.5(m, 24H), 4.0–4.4(m, 6H), 4.8(s, 1H).

EXAMPLE 17

To 200 ml of n-hexanol were added 10.0 g of 2-keto-L-gulonic acid monohydrate and 98 mg of concentrated sulfuric acid, and the heating under stirring was conducted in an oil bath of 120° C. for 5 hours. The low-boiling substances were distilled off under reduced pressure, and the residue was dissolved in ethyl acetate. The solution was washed with water, dried over anhydrous sodium sulfate and freed of the solvent under reduced pressure to give 10.8 g of an oily substance. The product was identified as n-hexyl 2-keto-L-gulonate by the IR and NMR data as described below.

IR (neat) cm$^{-1}$: 3400, 1750.

NMR (CDCl$_3$) δ: 0.87(m, 3H), 1.0–2.0(br., 8H), 3.3–5.3(m, 11H)

To 100 ml of acetone were added 5.4 g of n-hexyl 2-keto-L-gulonate and 51.2 mg of cupric chloride.dihydrate, and the reaction and the after-treatment were carried out by the procedures similar to those as described in Example 9 to give 6.09 g (87.5%) of n-hexyl 2,3:4,6-di-O-isopropylidene-2-keto-L-gulonate.

Melting point, an oily substance.

IR (neat) cm$^{-1}$: 1760 sh., 1748.

NMR (CDCl$_3$) δ: 0.85(m, 3H), 1.0–1.8(br., 8H), 1.28(s, 3H), 1.40(s, 6H), 1.52(s, 3H), 3.5–4.5(m, 6H), 4.82(s, 1H).

EXAMPLE 18

To 200 ml of cyclohexanol were added 10.0 g of 2-keto-L-gulonic acid monohydrate and 49 mg of sulfuric acid, and the heating was conducted in an oil bath of 100° C. for 9 hours. After completion of the reaction, the reaction solution was allowed to stand in a refrigerator, and the crystals which separated out were recovered by filtration, washed with a small amount of n-hexane and dried to give 6.7 g of n-hexyl 2-keto-L-gulonate.

Melting point, 170°–173° C.

IR (KBr) cm$^{-1}$: 3430, 3300, 1737

NMR (DMSO-d$_6$) δ: 1.0–2.1(br., 10H), 3.2–3.7(br., 4H), 4.0–6.3(br., 6H).

To 100 ml of acetone were added 5.0 g of cyclohexyl 2-keto-L-gulonate, 50.6 mg of 48% hydrobromic acid and 12 mg of cupric oxide, and the reaction and the after-treatment were carried out by the procedures similar to those as described in Example 9 to give 5.68 g (88.5%) of cyclohexyl 2,3:4,6-di-O-isopropylidene-2-keto-L-gulonate.

Melting point, an oily substance.

IR (neat) cm$^{-1}$: 1760, 1740.

NMR (CDCl$_3$) δ: 1.35(s, 3H), 1.44(s, 6H), 1.53(s, 3H), 1.3–2.1(br.,10H), 4.0–4.35(m, 5H), 4.80(s, 1H).

EXAMPLE 19

A mixture consisting of 50.0 g of 2-keto-L-gulonic acid monohydrate, 52.0 g of benzyl alcohol and 844 mg of 48% hydrobromic acid was allowed to react at 70° C. for 3 hours. After the addition of a small amount of pyridine, water and toluene were added to the reaction mixture, which was then shaken in a separating funnel. After the toluene layer was removed, the water layer was extracted with 500 ml of ethyl acetate, and the extraction procedure was repeated twice with 100 ml each of ethyl acetate. The ethyl acetate extracts were combined, dried (Na$_2$SO$_4$) and freed of the solvent under reduced pressure to give 10.3 g of crude benzyl 2-keto-L-gulonate.

Melting point, 105°–107° C. (recrystallized from ethyl acetate).

IR (KBr) cm$^{-1}$: 3450sh., 3360, 3300sh., 1750sh., 1740.

NMR (DMSO-d$_6$) δ: 3.47(br., 5H), 4.6–5.1(br., 3H), 5.18(s, 2H), 6.56(br., 1H), 7.38 (s, 5H).

Elemental analysis (%), for C$_{13}$H$_{16}$O$_7$ Calcd.: C, 54.93; H, 5.67. Found: C, 54.80; H, 5.80.

To 200 ml of acetone were added 10.0 g of benzyl 2-keto-L-gulonate and 112.3 mg of 57% hydriodic acid, and the reaction and the after-treatment were carried out by the procedures similar to those as described in Example 9 to give 9.69 g (75.6%) of benzyl 2,3:4,6-di-O-isopropylidene-2-keto-L-gulonate.

Melting point, an oily substance.
IR (neat) cm$^{-1}$: 1750.
NMR (CDCl$_3$) δ: 1.25(s, 3H), 1.40(s, 6H), 1.52(s, 3H), 4.0–4.4(m, 4H), 4.76(s, 1H), 5.25(s, 2H), 7.30(s, 5H).

EXAMPLE 20

To 200 ml of n-octanol were added 10.0 g of 2-keto-L-gulonic acid monohydrate and 49 mg of concentrated sulfuric acid, and the heating under stirring was conducted in an oil bath of 100° C. for 5 hours. After completion of the reaction, the low-boiling substances were distilled off under reduced pressure, and the residue was allowed to stand in a refrigerator. The crystals which separated out were recovered by filtration to give 5.3 g of n-octyl 2-keto-L-gulonate.

Melting point, 95°–96° C.
IR (KBr) cm$^{-1}$: 3400, 3250sh., 1730.
NMR (CDCl$_3$) δ: 0.9(m, 3H), 1.0–1.9(m, 12H), 3.4–5.5(m, 11H).

To 100 ml of acetone were added 5.0 g of n-octyl 2-keto-L-gulonate and 43.4 mg of antimony pentafluoride, and the reaction and the after-treatment were carried out by the procedures similar to those as described in Example 9 to give 7.23 g (87.3%) of n-octyl 2,3:4,6-di-O-isopropylidene-2-keto-L-gulonate.

Melting point, an oily substance.
IR (neat) cm$^{-1}$: 1760sh., 1748.
NMR (CDCl$_3$) δ: 0.81(t, 3H), 1.35(s, 3H), 1.43(s, 6H), 1.52(s, 3H), 1.1–2.0(br., 12H), 4.0–4.4(m, 6H), 4.8(s, 1H).

EXAMPLE 21

To 200 ml of n-dodecyl alcohol were added 20.0 mg of 2-keto-L-gulonic acid monohydrate and 196 mg of concentrated sulfuric acid, and the heating under stirring was conducted in an oil bath of 100° C. for 6 hours. After completion of the reaction, the solvent was distilled of under reduced pressure, and ether was added to the resulting residue, followed by the addition of activated carbon. The activated carbon was filtered off and the low-boiling substances were distilled off under reduced pressure to give crude n-dodecyl 2-keto-L-gulonate.

IR (neat) cm$^{-1}$: 3380, 1730.
NMR (CDCl$_3$) δ: 0.9(m, 3H), 1.0–2.0(m, 20H), 3.3–5.5(m, 11H).

To 100 ml of acetone were added 5.0 g of crude n-dodecyl 2-keto-L-gulonate and 127.0 mg of iodine, and the reaction and the after-treatment were carried out by the procedures similar to those as described in Example 9 to give 3.21 g (52.6%) of n-dodecyle 2,3:4,6-di-O-isopropylidene-2-keto-L-gulonate.

Melting point, an oily substance.
IR (neat) cm$^{-1}$: 1750.
NMR (CDCl$_3$) δ: 0.80(m, 3H), 1.34(s, 3H), 1.42(s, 6H), 1.50(s, 3H), 1.0–2.0(br., 20H), 4.0–4.5(m, 6H), 4.82(s, 1H).

EXAMPLE 22

To a mixed solution consisting of 250 ml methyl ethyl ketone and 150 ml of dichloromethane were added 20.0 g of 2-keto-L-gulonic acid monohydrate and 254 mg iodine, and the mixture was refluxed in a water bath of 68° C. for 8 hours. During this reaction, the refluxing solvent was dried with 40 g of Molecular Sieves 3A interposed between the reaction vessel and the condenser. After completion of the reaction, the low-boiling substances were distilled off under reduced pressure, and the oily residue was dissolved in benzene and then made strong alkaline by adding 20% aqueous caustic soda solution. After the separation of the benzene layer, the obtained water layer was neutralized and then made weekly acid (about pH 4) with hydrochloric acid. The extraction was conducted 3 times with 2 l (total) of ethyl acetate, the organic solvent layer was washed with water and dried over anhydrous sodium sulfate.

The sodium sulfate was filtered off and freed of the solvent under reduced pressure, the residue was solidified by allowing to stand at room temperature. The obtained solid was recrystallized from benzene-n-hexane to give 21.05 g (69.7%) of 2,3:4,6-di-O-sec-butylidene-2-keto-L-gulonic acid monohydrate.

Melting point, 78°–80° C.
IR (KBr) cm$^{-1}$: 3420, 1730, 1650.
NMR (CDCl$_3$) δ: 0.75–1.2(m, 6H), 1.25–1.55(q, 6H), 1.55–2.0(m, 4H), 4.0–4.8(m, 5H), 7.34(br., 1H).
Elemental analysis (%), for $C_{14}H_{24}O_8$ Calcd.: C, 52.49; H, 7.55. Found: C, 52.69; H, 7.59.

The concentrate which was obtained from the mother liquor after the recrystallization was chromatographed on a silica-gel column to give 2.68 g (11.5%) of 2,3-O-sec-butylidene-2-keto-L-gulonic acid.

Melting point, 108°–110° C. (recrystallized from ethyl acetate-n-hexane).
IR (KBr) cm$^{-1}$: 3400, 1746.
NMR (DMSO-d$_6$) δ: 0.8(t), 0.87(t) (the ratio of peaks 0.8 and 0.87 is about 2:1, 3H), 1.23(s), 1.33(s) (the ratio of peaks 1.23 and 1.33 is about 1:2, 3H), 1.35–1.8(m, 2H) 3.5–3.7(2H), 3.9–4.3(2H), 4.6–4.7(1H), 5–9(br., 3H).
Elemental analysis (%), for $C_{10}H_{16}O_7$ Calcd.: C, 48.39; H, 6.50. Found: C, 48.37; H, 6.53.

What we claim is:

1. A process for producing ketals of 2-ketogulonic acid or of its esters, which comprises reacting 2-ketogulonic acid or its esters with a ketone in the presence of a ketal formation catalyst selected from the following:
    (1) copper, or an oxide, hydroxide or salt thereof when used in the presence of hydrogen chloride or hydrogen bromide or cupric chloride and cupric bromide;
    (2) hydrogen iodide, hydriodic acid, a compound existing in the form of hydrogen iodide in the reaction system or a system liberating hydrogen iodide in the reaction system;
    (3) perchloric acid; or
    (4) antimony pentafluoride or antimony pentachloride.

2. The process according to claim 1, wherein the ester group is an alkyl having a carbon number of 1 to 18, a cycloalkyl having a carbon number of 4 to 8, an alkenyl having a carbon number of 3 to 14 or an aralkyl having an aryl group substituted by alkyl group with a carbon number of 1 to 4.

3. The process according to claim 2, wherein the alkyl is methyl, ethyl, n-butyl, hexyl, n-octyl or dodecyl.

4. The process according to claim 2, wherein the cycloalkyl is cyclohexyl.

5. The process according to claim 2, wherein the aralkyl is benzyl.

6. The process according to claim 1, wherein the ketone is one having a carbon number of 3 to 7.

7. The process according to claim 6, wherein the ketone is a dialkyl ketone having a carbon number of 3 to 6 or a cyclic ketone having a carbon number of 5 to 7.

8. The process according to claim 7, wherein the dialkyl ketone is acetone, methyl ethyl ketone or diethylketone.

9. The process according to claim 7, wherein the cyclic ketone is cyclopentanone or cyclohexanone.

10. The process according to claim 1, wherein the compound existing in the form of hydrogen iodide in the reaction system is an iodination agent or a Lewis acid containing iodine.

11. The process according to claim 10, wherein the iodination agent is iodine, iodine monochloride, iodine monobromide, iodine trichloride, N-iodosuccinimide, phosphorus triiodide or diphosphorous tetraiodide.

12. The process according to claim 10, wherein the Lewis acid containing iodine is titanium iodine or boron iodide.

13. The process according to claim 1, wherein the system is (1) a metal iodide and an acid, or (2) an iodination agent and a reducing agent.

* * * * *